United States Patent [19]

Wuchinich et al.

[11] 4,063,557
[45] Dec. 20, 1977

[54] ULTRASONIC ASPIRATOR

[75] Inventors: David G. Wuchinich; Alan Broadwin; Robert P. Andersen, all of New York, N.Y.

[73] Assignee: Cavitron Corporation, New York, N.Y.

[21] Appl. No.: 672,814

[22] Filed: Apr. 1, 1976

[51] Int. Cl.² .................. A61M 1/00; A61B 17/00
[52] U.S. Cl. ............................ 128/276; 128/303 R
[58] Field of Search ................... 128/303 C, 276

[56] References Cited
U.S. PATENT DOCUMENTS

| Re. 25,033 | 8/1961 | Balamuth et al. | 51/317 |
|---|---|---|---|
| 3,213,537 | 10/1965 | Balamuth et al. | 32/28 |
| 3,375,583 | 4/1968 | Blank et al. | 128/24 A X |
| 3,565,062 | 2/1971 | Kuris | 128/24 A |
| 3,589,363 | 6/1971 | Banko et al. | 128/276 |
| 3,809,977 | 5/1974 | Balamuth et al. | 128/24 A X |

Primary Examiner—Channing L. Pace
Attorney, Agent, or Firm—Philip Sperber

[57] ABSTRACT

Apparatus for the surgical removal of tissue is disclosed comprising a handpiece having a resonant vibrator with a magnetostrictive stack and connecting body encompassing a hollow elongated tool which is ultrasonically vibrated at its tip longitudinally to a peak to peak stroke of at least 0.005 inches at about 25,000 cps (25 KHz). A generator powers the vibrator and is automatically controlled at the frequency to maintain the resonant vibration. Aspiration is provided by suction through the hollow tool at its tip, and a manifold enclosing the tool end of the handpiece provides irrigation.

12 Claims, 4 Drawing Figures

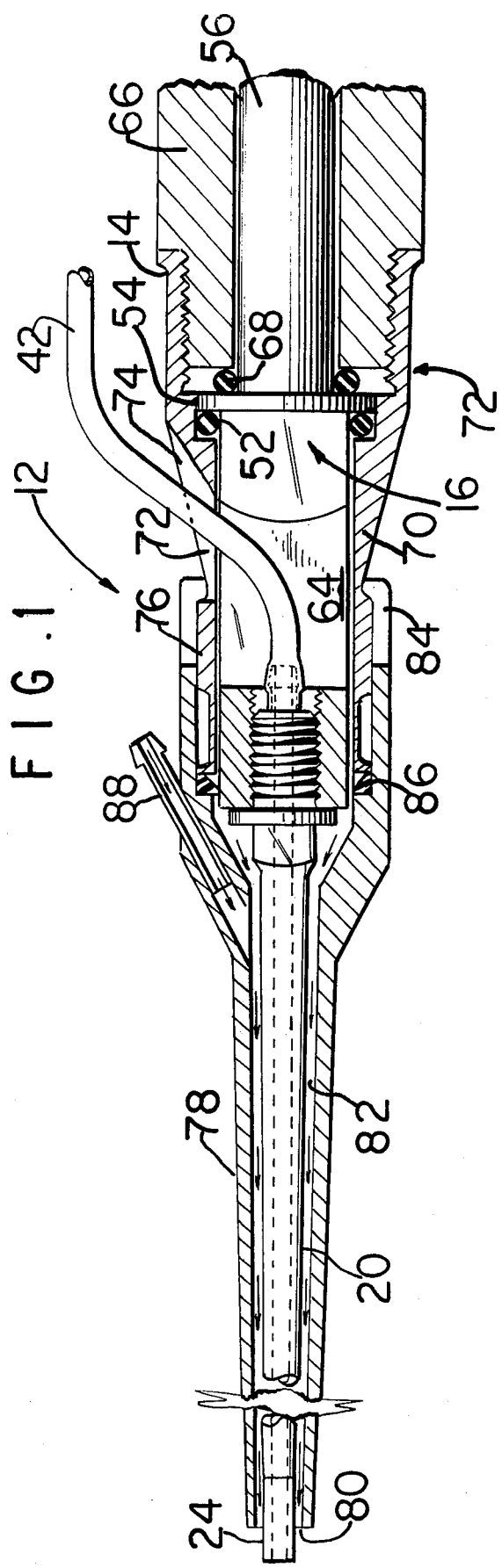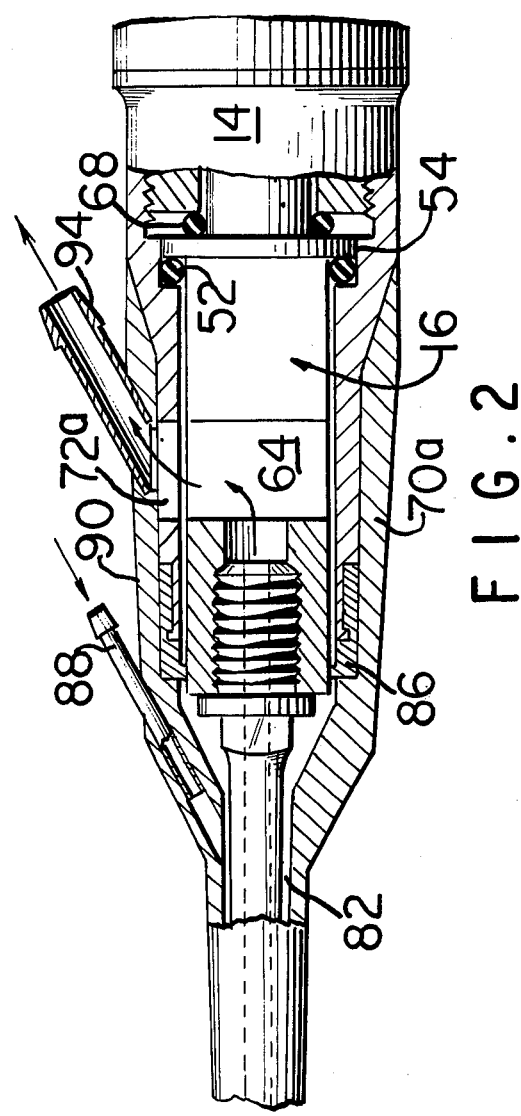
FIG. 1
FIG. 2

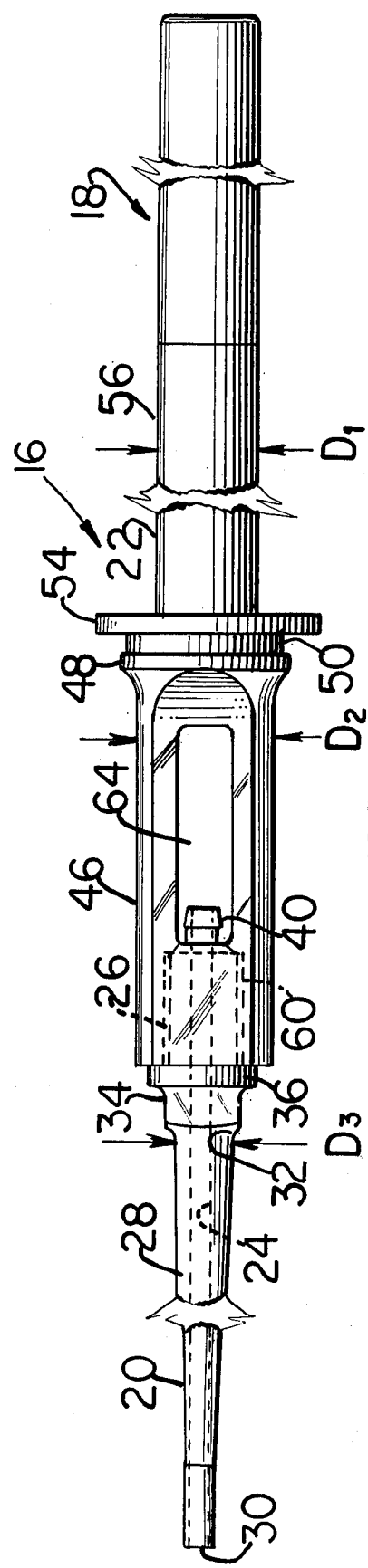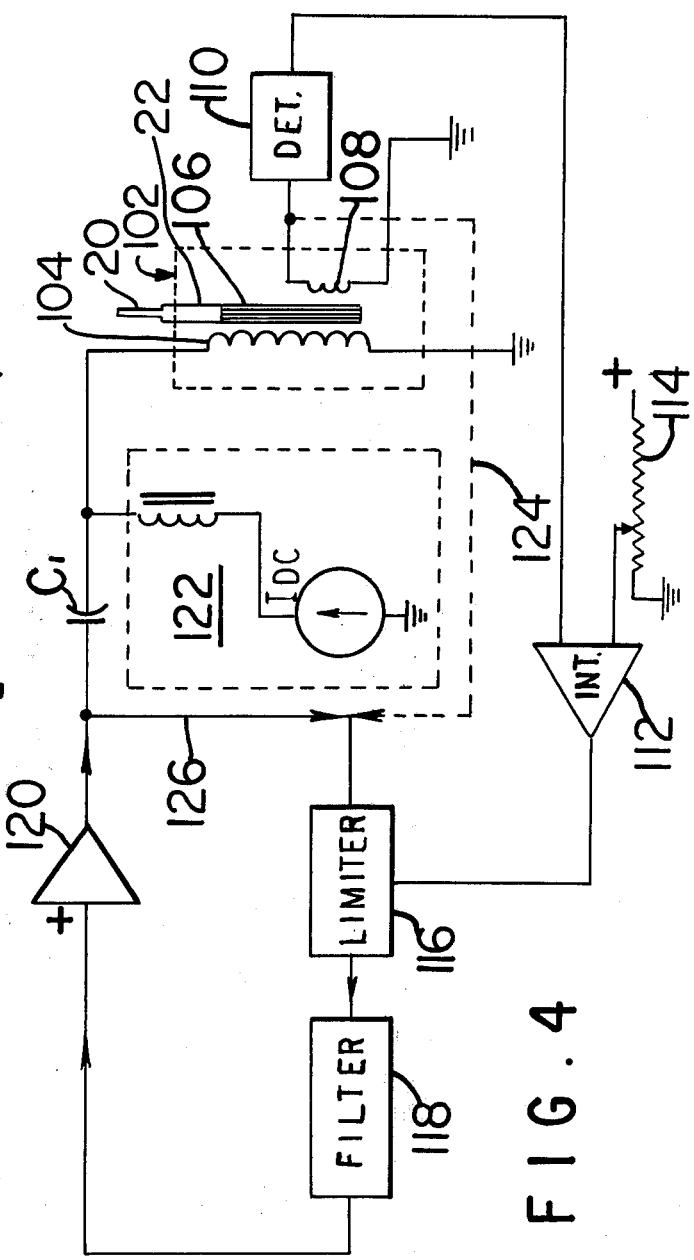

ULTRASONIC ASPIRATOR

BACKGROUND OF THE INVENTION

This invention is directed to an apparatus for ultrasonically disintegrating and aspirating tissue in a surgical operation. More particularly, this invention relates to an improved and novel surgical apparatus for disintegrating and aspirating a wide range of body tissues. Use of ultrasonically vibrated surgical tools to remove various types of body tissues is well known in the art. Certain of these instruments are being commonly used in various surgical procedures such as in the removal of cataracts from the eye as illustrated by U.S. Pat. No. 3,589,363 issued June 29, 1971 to A. Banko and C. P. Kelman. Other specialized ultrasonically driven surgical instruments have been patented, though the extent of actual use and practice is unknown. However, except for the ultrasonically driven dental prophylaxis unit (which is a widely accepted and successful instrument for cleaning the teeth professionally) and the use of ultrasonic instruments to surgically remove cataracts, the use of ultrasonically vibrated tools in the surgical removal of body tissues is not a common and accepted prodedure at present.

Several patents and patent applications are known which describe the use of such ultrasonically vibrated tools to remove tissues among which are U.S. patent application Ser. No. 555,474 filed Mar. 5, 1975 and assigned to the assignee of the present application, U.S. Pat. No. 3,526,219 issued Sept. 1, 1970, to L. Balamuth, and U.S. Pat. No. 3,565,062 issued Feb. 23, 1971 to A. Kuris. While the aforementioned patents describe various types of instrumentation for removing tissue, bodily tissues exhibit a wide range of mechanical characteristics; i.e., compliance, ranging from liquid to a relatively hard and brittle material such as bone. It is therefore unrealistic to assume that a single type of instrument can satisfactorily be used on all of the different types of tissue. We have found that while the apparatus and method described in the reference U.S. Patent Application is satisfactory for certain low-elasticity neurological tumorous tissue it is not satisfactory when employed on more elastic compliant tissue. Similarly it has been found that the instrumentation utilized in performing the cataract removal in accordance with the aforementioned U.S. Pat. No. 3,589,363 is quite unsuitable for removing neurological tumors and similar tissue. In regard to the instrumentation described in U.S. Pat. No. 3,526,219, it is difficult to ascertain the effectiveness of such instrumentation due to the broad nature of the teaching.

SUMMARY OF THE INVENTION

We have invented a novel surgical apparatus for disintegrating and aspirating tissue. The apparatus comprises in combination a handpiece having a resonant vibrator, generator means for electrically exciting the resonant vibrator in the ultrasonic frequency range, and means responsive to the vibrator for controlling the frequency of the generator means output. More particularly the resonant vibrator comprises an elongated hollow tool at its anterior end, a connecting member fixedly attached to the posterior end of the tool, and an electromechanical transducer attached to the other end of the connecting member and excited by the generator means, whereby ultrasonic vibrations are exhibited by the anterior end of the tool along its longitudinal axis having a peak amplitude (stroke) of at least 0.005 inches (5 mils). The tool preferably comprises a cylindrical and a conical section. The electromechanical transducer is preferably a magnetostrictive stack.

The generator means for electrically exciting the magnetostrictive stack comprises a generator having an output in the ultrasonic frequency range and means responsive to the level of stroke and resonant frequency of the transducer for automatically controlling the output frequency and power of the generator to substantially coincide with resonant frequency of the resonant vibrator, and maintain a desired stroke level.

An object of this invention is to provide a novel surgical apparatus employing an ultrasonically vibrating tool, having aspiration.

Another object of the present invention is to provide an ultrasonically vibrating tool having aspiration means which are isolated from the connecting member's mounting fixtures Still another object of the present invention is to provide an ultrasonically vibrating surgical tool wherein coolant fluid is separated and sealed of from the aspiration and irrigation means.

Yet another object of the present invention is to provide ultrasonic surgical apparatus for fragmenting, and aspirating highly compliant tissue containing blood.

It is yet another object of this invention to provide apparatus, having an ultrasonically vibrating surgical tool, which apparatus is automatically responsive to the resonant frequency and the desired vibratory stroke of the tool.

It is therefore also an object of this invention to provide apparatus for surgically removing tissue.

It is another object of this invention to provide apparatus for surgically disintegrating and aspirating tissue in an effective manner.

It is still another object of the present invention to provide surgical apparatus having an ultrasonically vibrating tool with a stroke of at least 5 mils (0.005 inch).

Yet another object of this invention is to provide ultrasonically vibrating surgical apparatus having automatic control of frequency and power in response to output of the vibrating surgical tool.

Still another object of this invention is to provide a high stroke ultrasonically vibrating surgical handpiece.

Another object of the present invention is to provide a conveniently held high power ultrasonic surgical tool having aspiration and irrigation.

Other objects and advantages of the present invention will be apparent to those skilled in the art from the description of the drawings and preferred embodiment which follows.

BRIEF DESCRIPTION OF THE DRAWINGS

FIG. 1 of the drawings is a sectional elevation of one version of the surgical handpiece according to this invention;

FIG. 2 is a sectional elevation of another version of the surgical handpiece;

FIG. 3 is an elevation of the resonant vibrator employed in the handpiece; and

FIG. 4 is a block diagram of the generator and handpiece combination according to the present invention.

DESCRIPTION OF THE PREFERRED EMBODIMENT

We have invented an improved apparatus for ultrasonically fragmenting and aspirating body tissue. The apparatus is embodied in a conveniently held handpiece 12, a cross-sectional view of which is shown in FIG. 1 of drawings, enclosing means for exciting a resonant member to vibrate in the ultrasonic range, including an aspirating tool vibrating at its tip in the ultrasonic frequency range at a longitudinal amplitude in excess of about 5 mils (0.005 inch).

To achieve such an effect in an instrument which can be conveniently held by a surgeon, a number of difficult obstacles must be overcome. One major obstacle is in transmitting excitation to an operating tool tip while at the same time such tip acts as the aspirating inlet to effect the surgical removal of the undesired tissue.

We have discovered that in order to surgically remove a broad enough range of compliant tissue that the surgeon is apt to encounter, an instrument which vibrates longitudinally in the range of at least 5 mils at about 25 KHz is necessary. At the same time as the tip is ultrasonically vibrating it is desirable to also apply aspiration to the affected tissue. A number of prior art issued patents such as previously mentioned do teach the application of aspiration together with an ultrasonic vibrating tool tip to remove body tissue. However, it has been found that except in specific instances where the particular tissue is readily susceptible to ultrasonic disintegration such as cataracts, it has been difficult to provide an ultrasonically vibrated tool to effectively remove tissue exhibiting a wide range of mechanical properties (i.e., compliance) which the surgeon may encounter in an operation. Thus, if the ultrasonic instrument was not adaptable to the range of tissue ordinarily encountered during specific types of operations, the instrument may have to be discarded for particular operations and is therefore an inconvenience during the operation. It is clearly recognized that to be acceptable to the surgeon, an instrument must be sufficiently rapid and selectively effective against the various types of tissue the surgeon is desirous of removing.

In particular, where highly compliant tissue mixed with blood is aspirated, there is the increased likelihood of occlusion of the aspiration conduit due to the coagulation of the blood. It is therefore desirable to provide as large an aspiration path as possible. This is to avoid clogging or occlusion of the aspiration path due to the increasing coagulation of the blood tissue mixture being aspirated. In addition, vibration apparently acts to increase the rate of coagulation. Therefore, the aspiration path or conduit should preferably have minimal changes of direction of flow and where such changes are required, they should be as gentle as possible. Further pockets of low flow velocity are also to be avoided.

Referring to FIG. 1 of the drawings where the surgical instrument 12 is shown in sectional elevation and comprises a tubular handpiece 14 and an elongated resonant vibrator 16 inserted therein and projecting out to the front part of the handpiece, as the instrument is held and manipulated by the surgeon in one of his hands, the size and weight of the handpiece is limited by the ability of the hand to delicately grasp and manipulate the instrument. For this purpose, the outside diameter of the handpiece should not exceed about 1.5 inches (3.7 cm) in overall diameter and a diameter of about 1 inch (2.5 cm) is preferred.

Referring now to construction of the resonant vibrator 16, the vibrator is basically a mechanical vibrating system mounted in the handpiece. The vibrating system is divided into a transducer; i.e., a magnetostrictive stack composed of nickel alloy sandwich such as is taught in U.S. Pat. No. Re25,033 and is well known in the art. Electrical oscillating current supplied to the winding of the coil induces mechanical oscillations in the stack, such oscillations being at the resonant frequency and having a maximum practical peak-to-peak stroke (amplitude) of about 1 thousandth of an inch (1 mil) at a frequency of about 25 KHz. As a practical matter due to limitations imposed by the state of the art, as frequency increases in the ultrasonic range, the stroke that one is able to obtain in the transducer is reduced.

Further, it is well known in the art that if one desires to take the available stroke from the transducer and vary the stroke, various design parameters are available for the design of an ultrasonic mechanical transformer. The design of such a transformer which is fixedly attached to the transducer magnetostrictive stroke is taught, for instance, in the aforementioned U.S. Pat. No. Re25,033.

Finally, the design of the transformer section must include and yield the preferred characteristics at the output portion of resonant vibrator. In this regard the output portion of the vibrator must vibrate ultrasonically with a desired stroke (peak to peak) of at least 0.005 inch (5 mils) while simultaneously functioning as an aspirator inlet. The output portion must also, for surgical requirements, be rather long and slender, while for aspiration purposes it is preferred to have as large a cross-sectional flow area as possible to thereby minimize the possibility of occluding the aspiration conduit.

Prior art hand-held commercial instruments, either providing irrigation or aspiration through the ultrasonic output end, have generally had strokes of less than 0.003 inch. Even this level of stroke is difficult to achieve at 25 KHz in a production instrument. The resonant vibrator output according to the present invention is (commercially capable of producing a stroke in the range of at least 5 mils and preferably from 5 to 16 mils at about 25,000 cps.

An acceptable ultrasonically vibrated surgical handpiece capable of such an output; i.e., a stroke of at least 5 mils at 25 KHz, has not been achieved, whereas we have invented such as described herein.

FIG. 3 of the drawings illustrates a preferred version of the resonant vibrator 16 having the magnetostrictive stack 18 at one end, a tool 20 at the forward end, and a connecting member 22 intermediate the tool 20 and the stack 18. For purposes of description, the tool encompasses that portion of the vibrator having an aspiration conduit 24 axially located therethrough. The tool is also coincidentally a substantially unitary body, designed for replacement as required and attached to the connecting member by a male threaded insert 26 at its posterior end. The preferred tool comprises an elongated hollow tube 28 at its anterior end, being about 0.09 inch at its tip 30 with a uniform outside diameter for about 0.65 inch and then tapering uniformly to an outside diameter of about 0.14 inch over a length of about 2 inches to fillet 32, where it is machined into a hexagonal neck 34 of about 0.19 inch. The neck 34 is connected to a circular rim 36 of about 0.3 inch diameter and 0.05 inch thickness. From the rim 36, the previously described male threaded insert 26, which is about ¼ inch long with an O.D. of about 0.21 inch, extends rearwardly and is chamfered at its end. The threaded insert 26 is necessarily a relatively large sized thread, being preferably a No. 12 screw thread, in order to withstand the extreme stresses present. Axially extending from the rearward end of the insert 26 is a nipple 40 having a necked-in outer surface for receiving and retaining an aspiration tube 42. The hollow aspiration conduit 24 extends the whole length of the tool and has a uniform internal diameter (I.D.) of preferably about 0.06 inch. Preferably the tool is made of a biologically compatible metal having a low characteristic acoustic impedance such as titanium or an alloy thereof.

The above-described tool 20, while susceptible to various modifications, necessarily must have an elongated tubular end having as small an outside diameter as is practical. Furthermore, since the tool tip 30 is to vibrate ultrasonically with a stroke in excess of 0.005 inch (5 mils), the tubular portion of the tool is tapered over most of its length to preferably reduce the stress to which the metal is subjected. Finally, and importantly, the tool in terms of its length and its distributed mass is dynamically a part of the resonant vibrator 16 which can magnify the 0.001 inch (1 mil) stroke input induced in the magnetostrictive stack 18 to in excess of a 5 mil output at the tool tip.

The connecting member 22 according to the present invention is a unitary metal structure also dynamically a part of a resonant vibrator which serves to connect the stack 18 to the tool 20 and, more importantly, to serve to transmit and modify the stroke as it is dynamically transmitted from the stack to the tool. Ideally the connecting member should be as wide as possible in contrast to the tool tip, as such a relative diameter increases the magnification, M, of the output stroke as much as possible at the tool tip in conformity with the following equation:

$$M = \sqrt{K_1 \frac{D_1^2}{D_2^2} + K_2 \frac{D_1^2}{D_3^2}}$$

where $K_1$ and $K_2$ are constants dependent on the lengths of the various elements and their material properties and $D_1$, $D_2$, and $D_3$ are the effective cross-sectional characters of the connecting member and tool as shown in FIG. 3 of the drawings. It is therefore readily apparent that the greater the diameter $D_1$ is in relation to diameters $D_2$ and $D_3$, the greater is the magnification M that is obtained. The node of motion of the resonant vibrator is located in the vicinity of flange 54, with the diameter $D_1$ of the connecting member being on the input side of the node and the diameters $D_2$ and $D_3$ being on the output side. But, as the portion 46 of the connecting member, which is defined by $D_2$ as the effective diameter, comprises the aspiration path communicating with the hollow tool, it is desirable to maintain the stroke level in this area as small as possible. If such connections are made, then the ratio of diameter $D_1$ to diameter $D_2$ should be as small as possible. Such a requirement modifies the above equation where if $D_2$ is made much larger than $D_1$, M becomes equal to $$\sqrt{K_2 \frac{D_1^2}{D_3^2}}$$

Thus the dynamic constraints appear to dictate a large diameter connecting member in order to achieve high magnification of output stroke. Since the handpiece 14 in which the vibrator and its connecting member are mounted has a practical limit to its size, it being necessary for the surgeon to conveniently hold it in one hand and manipulate it accurately, it has been previously found difficult to achieve high magnification in such small instrumentation.

To achieve such magnification, the connecting member 22 is made of a metal having a high characteristic acoustic impedance or an alloy such as monel shaped as shown and described herein. The anterior portion 46 of the connecting member 22 has a cross-section of about 0.38 inch square and a length of about 1.2 inches where it flares out to a circular rim 48 with a diameter of about 0.46 inch. The rim 48 forms the forward edge of an annular cutout 50 of about 0.435 inch diameter, which cutout 50 acts to retain for a first O-ring 52. The circular flange 54 serves as the rearward boundary of the cutout and functions to position the vibrator 16 in the handpiece 14 as will be hereafter described.

The rearward part of the connecting member is a solid circular rod 56 of about 0.28 inch in diameter and about 2 inches long, the posterior end of which is soldered, brazed, welded or otherwise fixed to the forward end of the magnetostrictive stack 18.

The anterior portion 46 of the connecting body has an axially located internally threaded bore 60 being sized to receive the full length of the male threaded insert 26 of the tool. The bore can have a shoulder against which the chamfered end of the threaded insert 26 stops under a predetermined torquing force. A large rectilinear slot 64 is located in the connecting member adjacent the end of the borehole and the tool's nipple extends into the opening formed by the slot. The aspiration tube 42, shown in FIG. 1, is thereby free to mate with the nipple in the opening thus formed by the slot without the necessity of a sharp radius being applied at the joint to either the aspiration tube or the conduit.

Referring again to FIGS. 1 and 2, where the resonant vibrator is shown mounted in the handpiece, the handpiece has a suitable wound coil (not shown) for exciting the magnetostrictive stack, and attached to a cable through which electrical power and signal conductors and cooling fluid are brought to the handpiece. The tubular part of the handpiece comprising a housing 80 has an opening through which the connecting member and stack are inserted. The housing 66 is undercut and externally threaded at its forward end. A second O-ring 68 is mounted on the rod 56 and is positioned between the housing's forward end and the flange 54 upon assembly of the handpiece.

The two O-rings 52 and 68 thus effectively seal the anterior portion of the connecting member forward of the flange from the internal volume of the handpiece enclosing the stack and containing the various electrical wiring and coolant supply lines in the handpiece.

A molded retainer 70 is positioned over the connecting member 22 and has an internally threaded cap 72 which is attached to the housing forward end. Internally forward of its cap, the retainer 70 is molded with a stepped internal diameter to fit over the first O-ring 52 in compressive contact and over the adjacent flange 54 with some minor clearance. The anterior portion of this stepped internal diameter is hexagonal in cross-section to enclose the anterior portion 46 of the connecting member, but with some minor clearance. Exteriorly the retainer 70 is molded with a dorsally located opening 74 through its wall adjacent the connecting member's slot. The opening 74 provides access for surgical grade plastic tubing 42 to connect to the tool nipple 40. The size of the opening and the slot is adequate so that the radius of curvature is gentle, thereby offering less resistance to aspirated blood containing tissue and lessening the possibility of occlusions occurring.

FIGS. 1 and 2 also illustrate two versions of an irrigation manifold 78, each version having a similar hollow truncated cone surrounding and spaced from the tool to provide an annular irrigation channel 82 having an annular nozzle 80 about ⅛ inch posterior to the tip of the tool. The flow of sterile irrigation fluid through the channel 82 has an effect on the tool output acting to dampen the vibration somewhat while importantly at the same time serving to cool the tool over most of its actual length.

The version of the manifold 78 illustrated in FIG. 1 widens posteriorly to fit over the retainer 70. The retainer in front of the opening 72 has a slightly larger outside width and depth, while the manifold's posterior end is molded with an interior lip 84. The manifold can therefore be slid over forward part of the retainer and when in proper assembled condition is held on the retainer by the lip 84.

The manifold 90 illustrated in FIG. 2 has no lip but rather is tightly fitted over the retainer. The manifold in the second version has a smaller opening into which an aspiration pipe 94 is inserted into the manifold's dorsal side and opens interiorly opposite the connecting member slot. The tool, though otherwise identical to that shown in FIGS. 1 and 2, is shown without its nipple. Aspirated material therefore flows from the hollow tool into the space provided by the slot 64 through an opening 70a in the retainer cap 72a and into the aspiration pipe 94.

An irrigation inlet pipe 88 is inserted fixedly into the cap's forward part and opened into the annular channel 82. Sterile surgical tubing (not shown) is connected to the irrigation as desired from a suitable source. A seal 86, preferably a silastic washer, is fitted over the anterior part of the connecting member adjacent a front edge of the retainer and serves to seal the irrigation fluid space from the space surrounding the connecting body (and serves as part of the aspiration fluid path in the handpiece shown in FIG. 2).

Supplying the irrigation fluid through the channel 82 provides three distinct advantages besides supplying irrigation fluid to the operative site. The irrigation fluid cools the vibrating tool and the material, blood, fluid and tissue being aspirated through the tool. If there is no such provision for cooling the high vibratory stroke output in excess of 0.005 inch of the tool would rapidly heat up from such intense vibration and weaken or damage the tool. Heat would also add to the rate of coagulation of blood being aspirated through the tool. Reducing the tool temperature thus reduces the possibility of occlusions. The irrigation fluid also wets the aspirated tissue, aiding in aspiration thereby. Further, it protects tissue not in contact with the tip.

The resonant vibrator according to the present invention has been found to resonate effectively in a rather narrow frequency band. Further, the actual frequency at which the vibrator effectively operates fluctuates during the course of an operation. It is not only inconvenient but also difficult and inefficient for an individual to continue manual tuning of the frequency during an operation. Accordingly, a novel and improved generator is described herein as part of this invention. A generator powers the handpiece by developing in the wound coil an alternating or oscillating current in a high frequency feedback loop of sufficient power oscillating at the required frequency to develop an oscillatory magnetic field exciting the magnetostrictive stack and converting electrical energy into mechanical energy. If the electrically powered frequency is not sufficiently coincident with the resonant frequency band of the resonant vibrator, energy transfer to the vibrator will be inefficient and the output of the vibrator will be limited to less than the desired stroke by its inherent characteristics. To achieve effective energy transfer at a sufficient vibratory level, the frequency and amplitude are regulated in interlocking control loops as described herein.

More particularly, attention is now directed to FIG. 4 of the drawings where the ultrasonic generator and handpiece block diagram is shown. The handpiece 102 comprises schematically an excitation coil 104, magnetostrictively exciting a resonant vibrator stack 106 as previously described (see reference 18 in FIG. 3). Once the vibratory frequency is established in the high frequency loop, the actual vibration in terms of the stroke of the vibrator is picked up by a secondary winding pickup 108 in the handpiece 102, and converted into a voltage equivalent of the stroke output by an envelope detector 110. The signal from the detector 110 is applied to an error integrator 112 mounted in the generator. The integrator 112 also has a reference input from a potentiometer 114 which is set by the operator to a desired stroke setting. The integrator 112 develops an output signal related to the difference between the stroke setting input as the reference signal and the voltage signal developed by the detector as a result of actual stroke of the vibrator. The output signal from the integrator 112 is the control signal to a variable limiter 116. The limiter 116 is in a high frequency feedback loop with, and picks up the output of, a transconductance amplifier 120. The output of the transconductance amplifier is the power input to the handpiece generating the voltage at the desired frequency for powering the magnetostrictive stack. The limiter 116 and a low Q active filter 118 are in the high frequency feedback loop to the transconductance amplifier, while the limiter 16 acts as a control for the control level feedback loop.

The limiter 116 takes the voltage output signal of the amplifier and modifies the limiter output level according to the control signal from the error integrator; i.e., it controls or limits voltage output in response to the control signal from the integrator. Also placed in the high frequency feedback loop between the limiter 116 and the amplifier is the filter 118 which functions as an active band pass filter. Thus, the filter 118 passes through only the fundamental component of the output from the limiter and, by doing so, prevents the amplifier (i.e., the generator), from operating in spurious modes, and generating undesired frequencies. The filter further acts to modify, if necessary, the signal to a more nearly sinusoidal type output. Alternatively the high frequency feedback loop may be varied to connect the limiter input via conductor 124 to the pickup 108 output and delete conductor 126. This latter variation allows automatic frequency control under high mechanical loading of the resonant vibrator.

The output of the generator; i.e., the transconductance amplifier 120, is applied through a D.C. biasing circuit 122 which is required in exciting a magnetostrictive transducer. The D.C. biasing circuit 122 thus acts to establish the required D.C. current in the excitation coil 104 to excite the stack as is well known in the art. Thus the generator and handpiece comprise two feedback loops. One feedback loop, the high frequency loop, comprises the amplifier, the limiter, and the filter, which is self-oscillating at a frequency determined by its phase shift including the impedance of the handpiece. The other feedback loop, the stroke level feedback loop, comprises the pickup, the detector, and the integrator, which inputs to the limiter to control the voltage level and thereby the stroke level of the vibrator. The output level of the amplifier is thus controlled in response to the level of sensed output. This output is fed back in a stroke level feedback loop through the integrator where it is compared to a preset desired level, and the difference from such comparison acts in the high frequency feedback loop to control the amplifier output to obtain the desired stroke level. A continued high stroke output at the tool tip is thus obtained. The frequency of the amplifier is automatically determined by the phase shift of the various active elements of the frequency feedback loop including the handpiece coil. As the resonant vibrator exhibits a narrow resonant frequency band, and can rapidly alter electric phase, it thereby effects the impedance at the handpiece coil 104. This impedance directly effects the phase shift of the amplifier and controls frequency in the high frequency feedback loop.

Having thus fully described our invention and wishing to cover those variations and modifications which would be apparent to those skilled in the art but without departing from either the spirit or scope thereof, we claim:

1. Apparatus for surgically removing tissue comprising in combination
    a handpiece,
    a resonant vibrator mounted in said handpiece, said vibrator comprising a transducer for converting electrical excitation to mechanical vibrations, a connecting means fixedly attached to the anterior end of said transducer for transmitting and modifying the vibrations, and a tool at the other end of said connecting means,
    electrical excitation means mounted in said handpiece adjacent said transducer for inducing ultrasonic vibrations in said transducer,
    generator means for powering said electrical excitation means, and
    control means responsive to said transducer means output for adjusting and controlling the output of said generator means by varying the frequency of said ultrasonic vibrations.

2. The apparatus according to claim 1 wherein said control means comprises stroke pickup means mounted adjacent said transducer for converting the vibrating stroke of said transducer into an electrical signal indicative thereof; an error integrator electrically connected at one input thereof to said pickup means at the output thereof, stroke setting means connected to said integrator at another input thereto for adjusting and supplying a reference signal to said integrator indicative of the desired stroke of the resonant vibrator, and frequency control means responsive to the resonant frequency of said vibrator.

3. A device for surgically disintegrating and aspirating tissue comprising
    a handpiece,
    a resonant vibrator mounted in said handpiece, and having a hollow elongated tool extending out from said handpiece, a connecting member at the other end of said tool, and a transducer connected to the posterior end of said connecting member,
    electrical excitation means mounted in said handpiece adjacent said transducer for exciting said transducer to vibrate in the ultrasonic frequency range, with a longitudinal stroke of at least 0.005 inch peak to peak, and
    aspiration means for applying suction through said hollow elongated tool communicatingly connected to the posterior end of said hollow tool, and
    automatic control means responsive to the level of said resonant vibrator for adjusting and controlling the output of said electrical excitation means in reference to a predetermined stroke level setting by varying the frequency of said resonant vibrator.

4. The device according to claim 3 wherein said connecting member comprises an anterior portion having a longitudinally extending slot therethrough, and an axially located bore extending to the anterior end of said slot, said tool being fixedly secured posteriorly in said bore, and having aspiration connecting means axially extending from the posterior end of said tool for connecting an aspiration conduit thereto.

5. The device according to claim 4 which additionally comprises irrigation means mounted on said handpiece for supplying sterile fluid to a point in the vicinity of the anterior end of said tool.

6. The device according to claim 3 wherein said connecting member comprises an annular flange positioned at about the nodal point thereof,
    said handpiece comprising a casing surrounding and spaced from said connecting member's posterior portion, and a retainer enclosing and spaced from said connecting member's anterior portion,
    said device additionally comprising a first elastomeric ring positioned on said connecting member's posterior portion and abutting said flange on its posterior face and said casing, and a second elastomeric ring positioned on said connecting member's anterior portion and abutting said flange on its anterior face whereby said first and second elastomeric rings elastically support and seal said resonant vibrator at about a nodal point thereof in said handpiece.

7. The device according to claim 5 wherein said irrigation means comprises a hollow elongated manifold sealingly fixed to the front of said handpiece and enclosingly spaced from said hollow elongated tool to provide an annular opening posteriorly of the tip of said hollow tool and fluid supply means communicatingly connected to said manifold for supplying fluid to said irrigation means.

8. The device according to claim 7 wherein said connecting member comprises an annular flange positioned at about the nodal point thereof,
    said handpiece comprising a casing surrounding and spaced from said connecting member's posterior portion, and a retainer enclosing and spaced from said connecting member's anterior portion,
    said device additionally comprising a first elastomeric ring positioned on said connecting member's posterior portion and abutting said flange on its posterior face and said casing, and a second elastomeric ring positioned on said connecting member's anterior portion and abutting said flange on its anterior face whereby said first and second elastomeric ring elastically support and seal said resonant vibrator at about a nodal point thereof in said handpiece.

9. The device according to claim 8 which additionally comprises a fluid seal between said connecting member's anterior portion and said manifold thereby sealing the space defining an aspiration path between said first elastomeric ring and said fluid seal, said manifold additionally having an opening opposite said slot in said connecting member whereby said aspiration path is in fluid communication with said manifold opening, said manifold opening having a means for sealingly attaching an aspiration conduit thereto.

10. The device according to claim 8 which additionally comprises a fluid seal between said connecting member's anterior portion and said manifold, said manifold having an opening therethrough opposite said connecting member's slot, said elongated hollow tool having a hollow nipple at its posterior end for removably connecting a flexible aspiration conduit to said nipple, said flexible conduit being adapted to pass through the opening in said manifold.

11. The device according to claim 3 wherein said transducer is a magnetostrictive stack.

12. The device according to claim 11 which additionally comprises automatic control means responsive to the level of stroke of said resonant vibrator for adjusting and controlling the output of said electrical excitation means by varying the frequency of said excitation means.

* * * * *